(12) United States Patent
Velidandla

(10) Patent No.: US 7,355,711 B2
(45) Date of Patent: Apr. 8, 2008

(54) METHOD FOR DETECTING AN END-POINT FOR POLISHING A MATERIAL

(75) Inventor: Vamsi Mohan Velidandla, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 293 days.

(21) Appl. No.: 11/173,212

(22) Filed: Jul. 1, 2005

(65) Prior Publication Data

US 2007/0004061 A1 Jan. 4, 2007

(51) Int. Cl.
*G01N 21/55* (2006.01)
(52) U.S. Cl. .................. 356/445; 356/600; 356/632
(58) Field of Classification Search .............. 356/630, 356/632, 445–448, 600; 382/168
See application file for complete search history.

(56) References Cited

U.S. PATENT DOCUMENTS

| | | | | |
|---|---|---|---|---|
| 4,479,848 A * | 10/1984 | Otsubo et al. | ............... | 356/445 |
| 6,031,615 A | 2/2000 | Meeks | | |
| 6,130,749 A | 10/2000 | Meeks | | |
| 6,198,533 B1 | 3/2001 | Meeks | | |
| 6,229,610 B1 | 5/2001 | Meeks | | |
| 6,268,919 B1 | 7/2001 | Meeks | | |
| 6,392,749 B1 | 5/2002 | Meeks | | |
| 6,514,775 B2 * | 2/2003 | Chen et al. | ..................... | 438/8 |
| 6,624,884 B1 | 9/2003 | Imaino | | |
| 6,665,078 B1 | 12/2003 | Meeks | | |
| 6,678,043 B1 * | 1/2004 | Vurens et al. | ........... | 356/237.2 |
| 6,704,435 B1 | 3/2004 | Imaino | | |
| 6,717,671 B1 | 4/2004 | Meeks | | |
| 6,751,044 B1 | 6/2004 | Meeks | | |
| 6,757,056 B1 | 6/2004 | Meeks | | |
| 6,781,103 B1 | 8/2004 | Lane | | |
| 6,947,587 B1 * | 9/2005 | Maeda et al. | ................ | 382/149 |
| 2002/0159626 A1 * | 10/2002 | Shiomi et al. | .............. | 382/145 |

* cited by examiner

*Primary Examiner*—Samuel A. Turner
*Assistant Examiner*—Juan D Valentin, II
(74) *Attorney, Agent, or Firm*—Caven & Aghevli LLC

(57) ABSTRACT

An optical surface analysis system for scanning the surface of a (silicon) wafer and detect if any residual material is still on the wafer surface in order to determine an appropriate end-point in a polishing process. An Optical Surface Analyzer (OSA), of the present invention, is generally used to identify composition, measure surface area, and measure thickness variations of thin film layers of material. The difference in optical properties (index of refraction) of different materials on the surface allows the system of the present invention to separate different materials on the wafer surface using the histogram plots generated by the OSA. This method is used to detect and make a quantitative assessment regarding the amount of residual material to be removed by the polishing process and, therefore, when an appropriate end-point has been reached in the polishing process.

14 Claims, 10 Drawing Sheets

METHOD FOR DETECTING AN END-POINT FOR POLISHING A MATERIAL

BACKGROUND OF THE INVENTION

1. Field of the Invention

The present invention generally relates to the field of removing a layer of material from a semiconducting wafer, and more specifically to the detection of an end-point for chemical mechanical polishing (CMP) of a semiconducting wafer by way of an optical surface analyzer (OSA).

2. Description of Background Art

Chemical Mechanical Polishing (CMP) is used in the semiconducting manufacturing process to flatten and/or remove a layer of material from the surface of wafers. The CMP process is used to planarize the surface of a coated and patterned silicon wafer. To control the CMP process engineers want to measure the amount of material removed from the metal region as compared to the oxide region. Since the oxide and the metal areas have different mechanical properties they will polish at different rates. It is desirable to detect when the polishing equipment has removed a layer of material (copper, for example) from the surface of the silicon wafer. This process is known as end-point detection.

The conventional technique for detecting the end-point for polishing materials involves processing die-to-die images to identify where the material (i.e. copper) residue is located. Typically a camera based imaging system will acquire an image of a die and compare it to a stored image taken on a perfectly clean die. Other techniques involve ellipsometry as well as profilometry to determine the effect of CMP on the surface. The drawbacks in performing a die-to-die match to determine end-point processing are apparent in the relatively slow processing time of this manual process. Also, the process of matching die-to-die images produces results that are qualitative in nature and limited to information regarding the uniformity of a polishing cycle. These methods are silent with regards to quantitative measurements pertaining to the amount a material has been over-polished or under-polished.

What is needed is a system and method for automated detection of the end-point in the process of removing a material by polishing and a quantitative analysis of the amount of material that is over-polished or under-polished.

SUMMARY OF THE INVENTION

The present invention overcomes the limitations of conventional methods by enabling the automated detection of the end-point in the process of removing a material by polishing. An optical surface analysis system is disclosed to scan the surface of a (silicon) wafer and detect if any residual material remains on the surface. The surface area of the residual material can then be calculated to track the removal process.

When a surface is scanned with an Optical Surface Analyzer (OSA), the image generated is proportional to the amount of light reflected from the surface. The difference in optical properties (index of refraction) of different materials on the surface of a sample (wafer) allows the system to separate materials on the wafer surface by analyzing the histogram plots generated by the OSA. The histogram of the pixels in an OSA image represent thickness variations and spatial distributions of the different materials on the wafer. Through analysis of the histogram, the present invention is used to detect and make quantitative assessments regarding the amount of residual material to be removed by the polishing process.

DETAILED DESCRIPTION OF THE INVENTION

Figure 1:
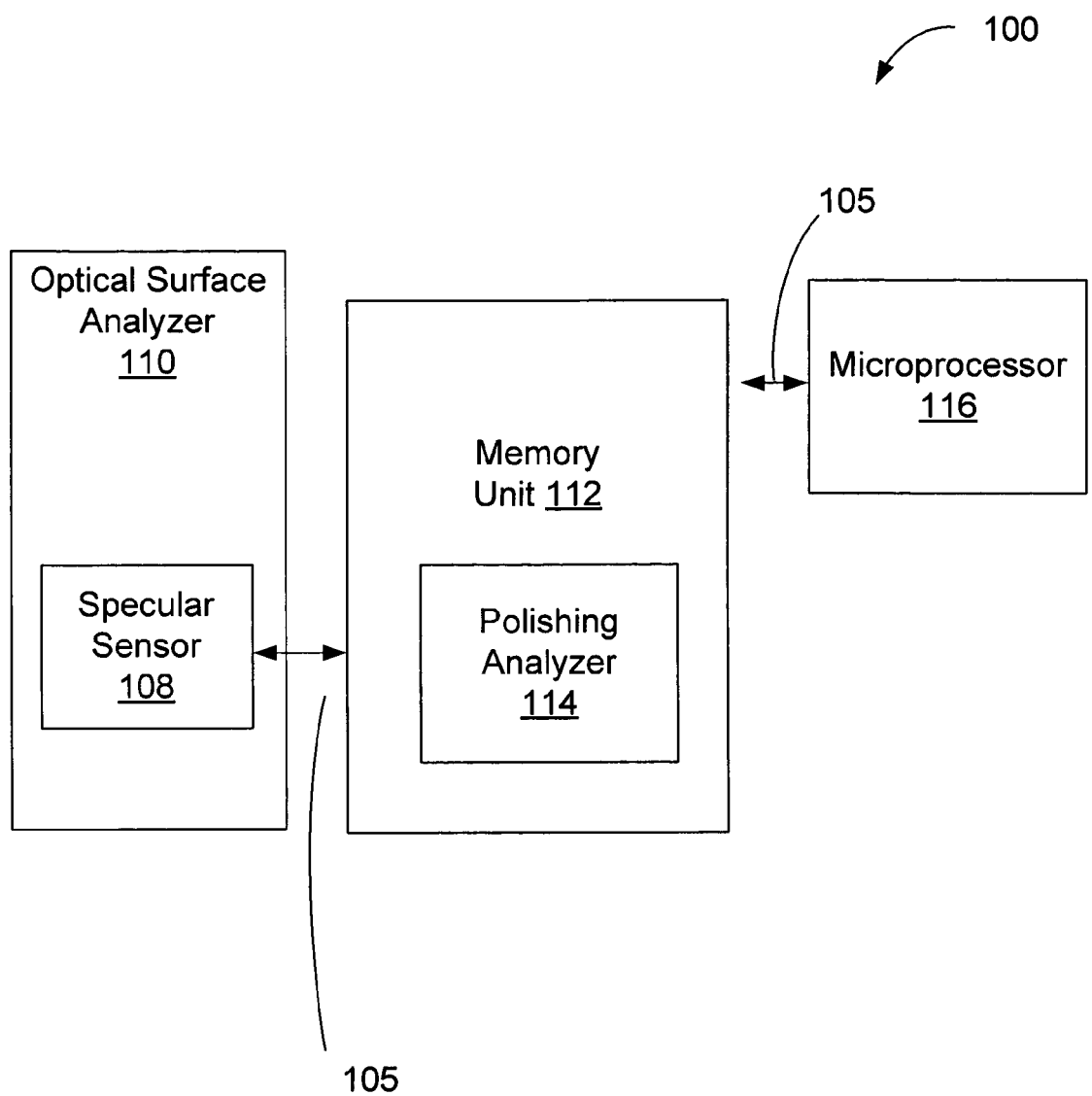
FIG. 1 is an illustration of a system for detecting the end-point in the process of removing a layer of material by polishing in accordance with an embodiment of the present invention.

A preferred embodiment of the present invention is now described with reference to the figures where like reference numbers indicate identical or functionally similar elements. Also in the figures, the left most digits of each reference number corresponds to the figure in which the reference number is first used.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

FIG. 1 is an illustration of a system 100 for detecting an end-point in the process for removing a first layer of material from an object by polishing according to an embodiment of the present invention. In this embodiment, an optical surface analyzer (OSA) 110 is provided with at least a specular sensor 108 for inspection of an object's surface by way of an optical scan. Output signals from specular sensor 108 are channeled to memory unit 112 through connection 105. Connection 105 consists of an analog to digital converter (ADC) which transfers the digitized signal to the computer via data acquisition cards connected to the motherboard of the computer. where a polishing analyzer 114 provides an end-point detection analysis. The polishing analyzer 114 is driven by microprocessor 116.

Figure 2:
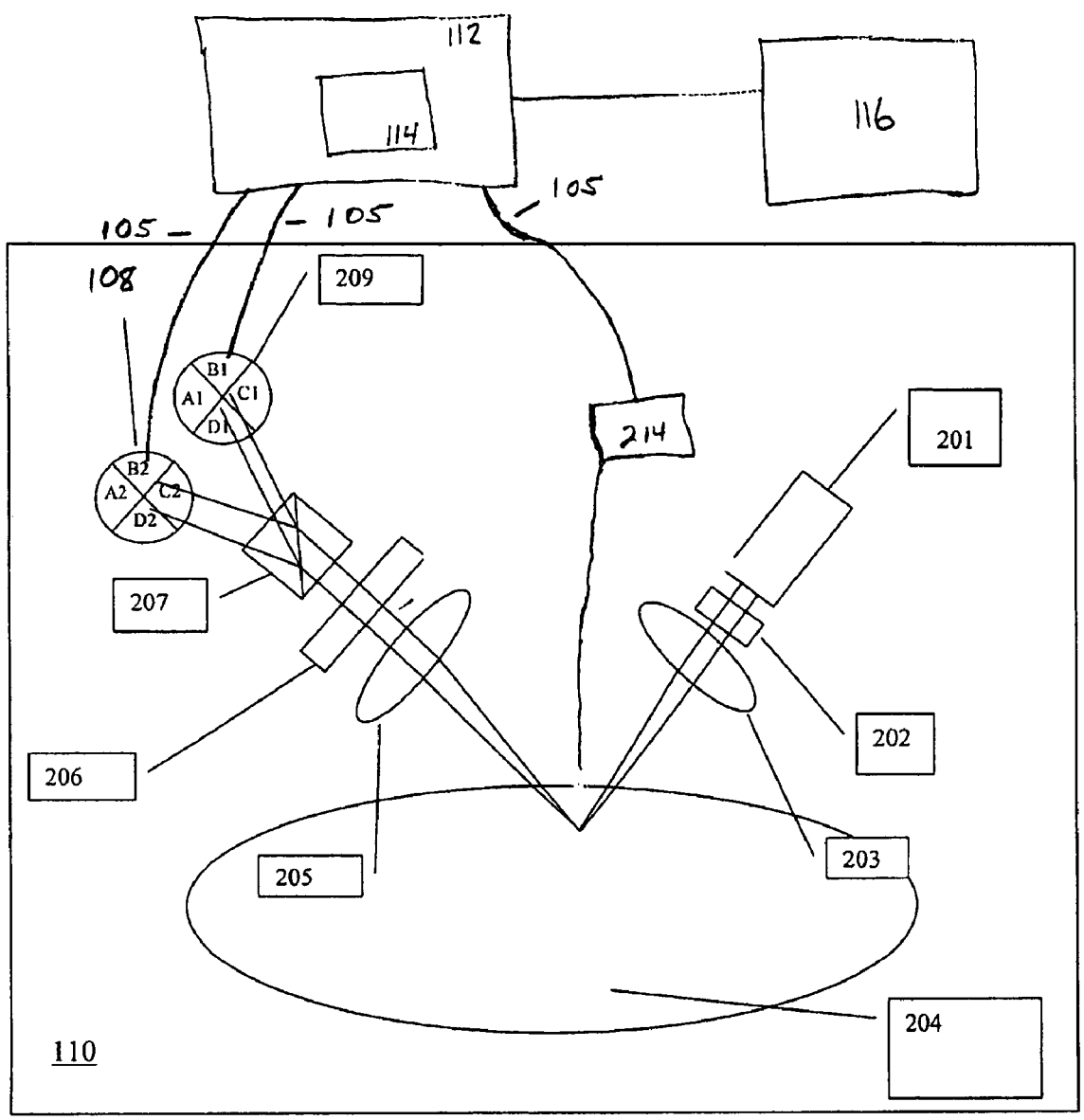
FIG. 2 is a detailed illustration of an optical surface analysis tool for detecting the end-point in the process of removing a layer of material by polishing in accordance with an embodiment of the present invention.

FIG. 2 is an illustration of an optical surface analyzer 110, according to an embodiment of the present invention, for detecting an end-point in the process for removing a first layer of material (not shown) from an object 204 by polishing. A laser diode 201 emits an electromagnetic signal toward the object 204 (i.e. thin film disk, silicon wafer, photonics wafer or glass substrate). In an embodiment the electromagnetic signal is a light signal having a wavelength of 780 or 655 nanometers (nm) although a wide variety of wavelengths can be used. The angle of propagation of the light signal can be any angle θ between zero and ninety degrees.

Laser diodes have an internal photodiode to monitor the laser output power. An embodiment of a feedback control circuit to control the optical intensity is to use such a photodiode, which is internal to the laser diode. This photodiode feeds back a control signal to negative feedback circuitry to control the intensity of the laser at a constant value. The photodiode that is used to control the laser intensity may be external to the laser. When an external photodiode is used, an external non-polarizing beam splitter is placed after the laser. This external non-polarizing beam splitter directs a sample of the laser onto the external photodiode. The signal from the external photodiode is used to feedback a control signal to negative feedback circuitry and thereby controls the laser intensity. Another means of keeping an approximate constant output power of the laser is to control the current of the laser diode, that is, run the diode laser in a constant current mode. The laser diode will exhibit a slow decrease in output power over a period of months. As long as the scan time is less than 5 or 10 minutes then the optical power output of the laser will remain constant during the scan. An advantage of this technique is its simplicity. Long-term drifts of the laser output power may be calibrated by first measuring a standard reflector and using this to normalize the measured signals. The value of the signal is first measured over the standard (known) reflector and then the object (disk or wafer) is measured. If there has been any drift of the standard reflector measurement then all the data is corrected for this amount of drift. As a result long-term drifts may be compensated even when operating in a constant current mode. The emitted light passes through the linear polarizer 202. The linear polarizer 202 improves the linear polarization of the laser light signal.

In an embodiment, the laser beam from the diode laser 201 passes through a linear polarizer 202, and a first focusing lens 203 and then strikes an object 204 (disk or wafer). Upon reflecting from the surface the beam passes through a recollimating lens 205, a quarter wave plate 206, and through a polarizing beam splitter such as Wollaston prism 207 which is rotated at 45° to the plane of incidence and onto two quadrant detectors 108 and 209. The specular signal is obtained by summing the signals from a first position sensitive detector 209 with the sum of the signal of a second position sensitive detector 108, times a constant κ:

$$\text{Specular signal} = (A1+B1+C1+D1) + \kappa^*(A2+B2+C2+D2)$$

Position sensitive detectors 108 and 209 (quadrant detectors) can serve as phase detectors, specular detectors, or topography measurement detectors. The outputs from the quadrant detectors are digitized by a conventional analog to digital converter and directed to the memory unit 112 of a microprocessor 116 (or conventional personal computer). The signals are then analyzed by polishing analyzer 114 to determine an appropriate end-point for polishing when removing a material from object 204. An avalanche photodiode, conventional PIN photodiode or photo multiplier tube 214, for example, detects the scattered component of the signal, according to another embodiment. The recollimated beam passes through a zero order quarter wave plate 206 that is used to adjust the polarization of the beam so that equal amounts of energy are directed into the quadrant photodetectors 108 and 209. According to an embodiment, both position sensitive detectors 108 and 209, and scatter detector 214, are coupled to memory unit 112 by way of connection 105. Connection 105 consists of an analog to digital converter (ADC) which transfers the digitized signal to the computer via data acquisition cards connected to the motherboard of the computer. A combination of signals from position sensitive detectors 108 and 109 and the scatter detector 214 can be further utilized in a detailed analysis of surface topography, defects, pits, mounds, stains, etc. as shown in U.S. patent application Ser. No. 10/754,275, which is incorporated by reference herein in its entirety.

The entire optical apparatus 110 is placed upon a stage that moves the apparatus 110 in the radial direction while a motor (not shown) rotates the object 204. In this manner the entire surface of the object 204 may be scanned for defects. An alternative embodiment for scanning the entire object 204 is to place the optical head or the object 204 on an x-y scan stage. The object 204 or the optical apparatus 110 is scanned in the x and y directions and in this manner the entire sample may be scanned for defects or topography.

When object 204 is scanned with the Optical Surface Analyzer (OSA) 110, an image is generated using signals reflected from the surface of the object 204. The amount of light reflected from the object's surface is dependent on the refractive index of the object as well as the thickness of any overlying material (i.e. a metallic material, like copper, overlying a silicon substrate in a semiconducting object). When dissimilar materials are adjacent to each other, OSA images appear with different reflectivity values.

Figure 3A:
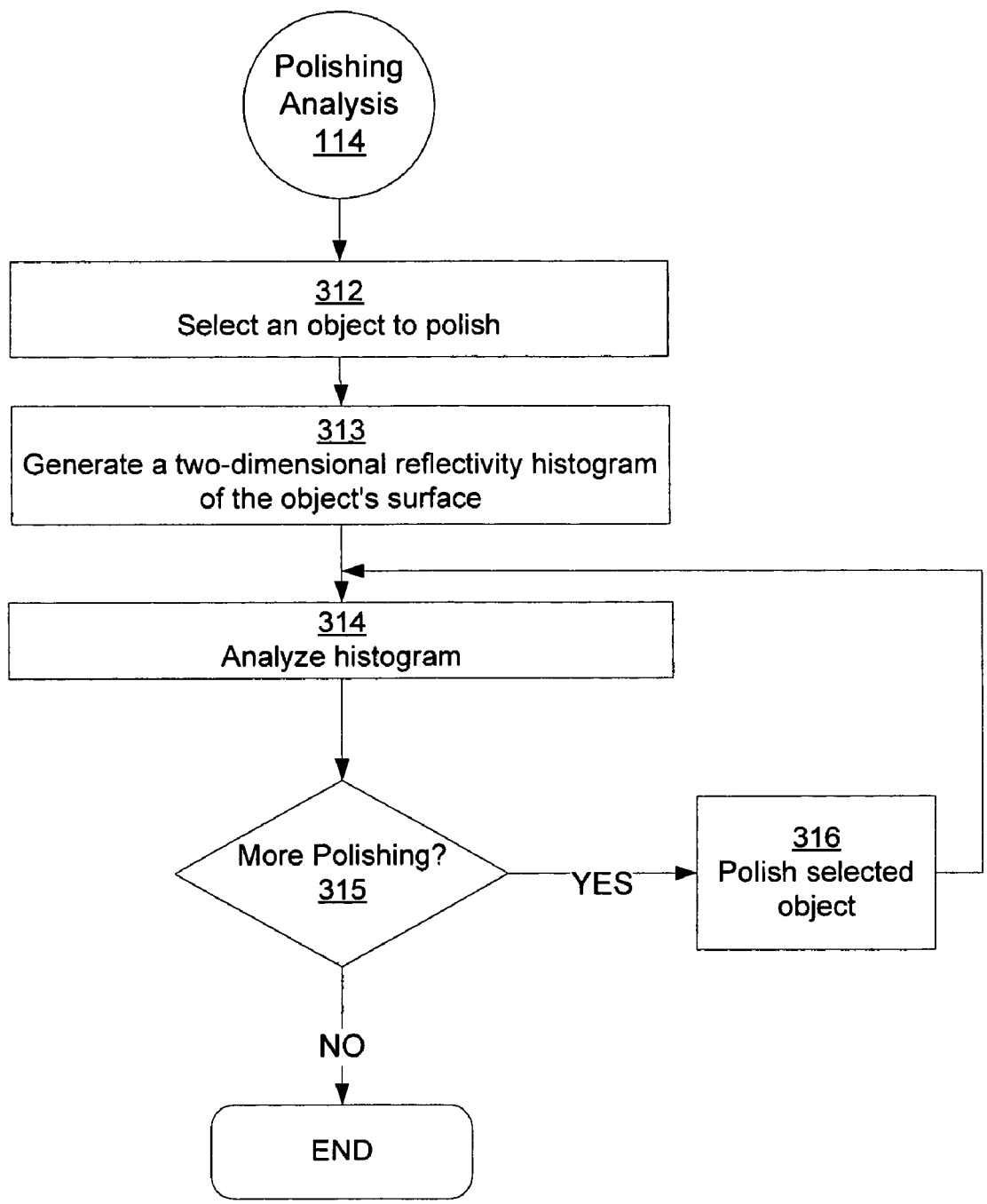
FIGS. 3A and 3B are logic flow diagrams illustrating a method for detecting the end-point in the process of removing a layer of material by polishing in accordance with an embodiment of the present invention.
Figure 3B:
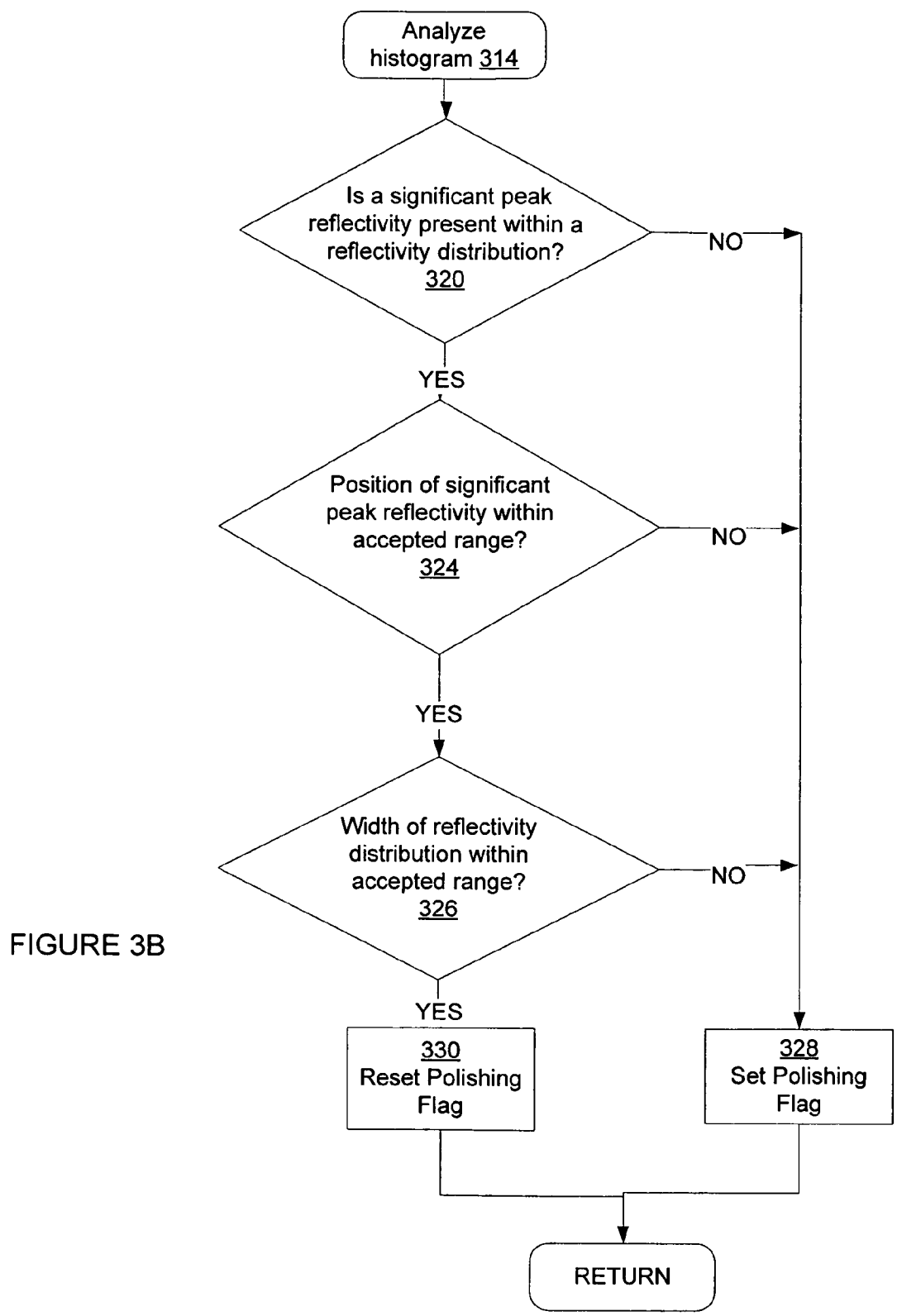
Figure 4A:
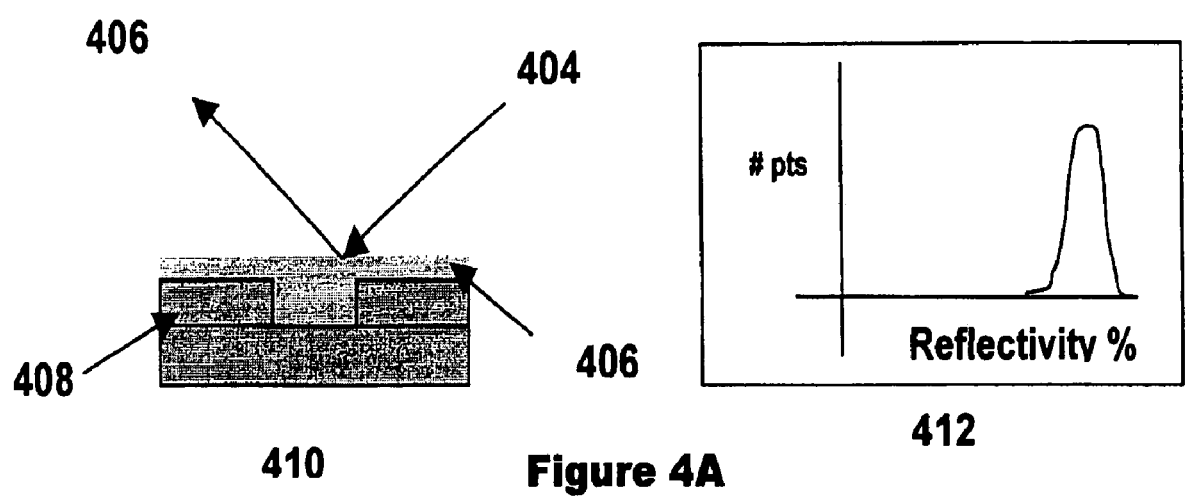
FIGS. 4A-4C are illustrations showing a quantitative correlation between residual wafer surface residue and peak reflectivity.
Figure 4B:
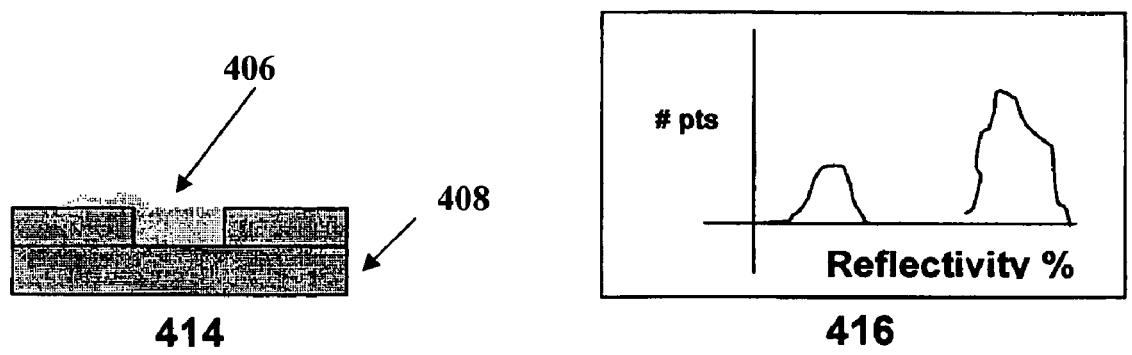
Figure 4C:
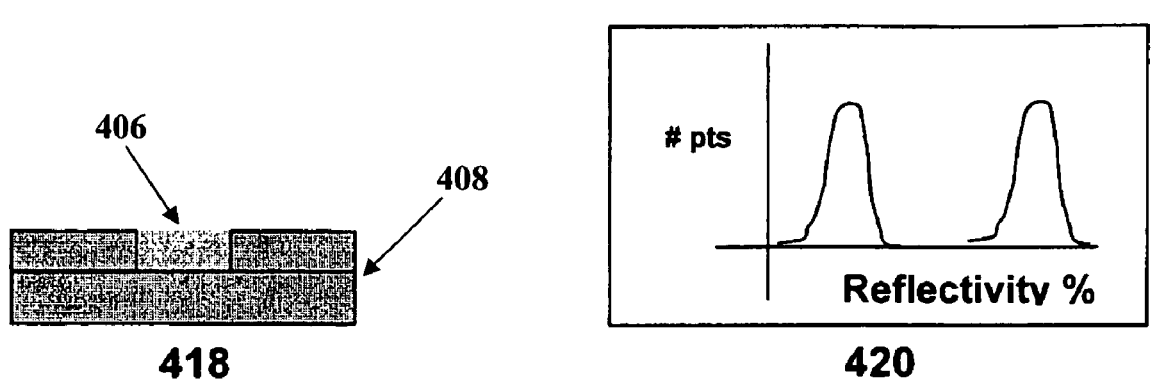

According to an embodiment of the present invention, as shown in FIGS. 3A and 3B, the polishing analyzer 114 selects 312 a sample to be polished and performs a detailed analysis 314 of the reflectivity image of the object's 204 surface generated by the optical surface analyzer 110. A reflectivity histogram (as seen in FIGS. 4A-C) is generated 313 from the pixels in an OSA image that can distinguish thickness variation and spatial distribution of any particular materials on the surface of the object 204. An analysis 314 of the reflectivity histogram of the object 204 provides different peak reflectivity distributions, for each material on the object 204, that can be characterized by their position and width (or thickness variation).

According to an embodiment, a phase histogram, a scatter histogram, or a topography histogram is generated and analyzed in a similar fashion as the embodiment described for analyzing the reflectivity histogram for a determining an end-point for polishing a material.

Polishing analyzer 114 determines whether to continue polishing or when an appropriate end-point has been reached by verifying if a polishing flag is set 315. When the polishing flag returns a negative response ("NO"), the analyzer 114 determines that an end-point to the polishing process has been reached. When the polishing flag returns a positive response ("YES"), the object is returned to the polishing apparatus (not shown) for further polishing. After polishing, the object's 204 reflectivity histogram is analyzed 314 for end-point detection. At least two determinations are needed to satisfy end-point detection, according to an embodiment of the present invention: verifying 320 the presence of a significant peak reflectivity within a reflectivity distribution of the reflectivity histogram; and determining 324 that the position of the significant peak reflectivity is within an accepted range. According to an embodiment, a reflectivity percentage within a distribution is considered to be a significant peak when it exceeds a certain minimum # of occurrences and when it is higher than the average of its two nearest neighbors on either side. Other data processing techniques such as curve fitting may also be utilized to find the significant peak on the histogram. Likewise, the position of a significant peak reflectivity located within a pre-set % of the accepted value is considered within an accepted range. The preset % will depend on the quality of finish required by the end user. Examples of materials that can be analyzed by an embodiment of the present invention are aluminum (71% reflective), copper (90% reflective), and silicon (28% reflective). There is no restriction on the type of materials or the thickness of the materials that can be analyzed with this method. The method will have limited scope if the two adjacent materials have very similar refractive indicies. This may be improved upon by using different angles of incidence or different wavelengths of incident illumination.

In the case that a significant peak is not verified 320 or the position of a significant peak is not within the acceptable range 324, a polishing flag is set 328 and the object 204 is returned to polishing 316 for additional polishing. According to another embodiment for analyzing the end-point of removing a material by polishing, the width of a reflectivity distribution in the histogram is determined to be within an accepted range 326. An accepted full width at half maximum for an embodiment of the present invention can be determined by the end user based on the materials being tested. For example, in the case of FIG. 5A, an acceptable full width at half-max may be 1%. For different materials and different processes, there might be different values of full width half max for each of the peaks.

According to an embodiment, in the case that steps 320 and 324 return an affirmative response ("YES"), the end-point flag is reset 330, and the polishing process is complete. According to another embodiment, in the case that steps 320, 324, and 326 return an affirmative response ("YES"), the end-point flag is reset 330, and the polishing process is complete. According to an embodiment, in the case that steps 320 and 324 return a negative response ("NO"), a polishing flag is set 328 and the object 204 is returned to polishing 316 for additional polishing.

In general, for a relatively successful CMP process, the peak reflectivity distributions are distinctly positioned within the histogram and the width about the significant peaks of the distributions is substantially narrow. In the case of under or over-polishing, the width around the unpolished material's significant peak is wider than the width around a significant peak under optimum polishing conditions. Also, extraneous significant peaks can be present in the histogram of an object that has been over or under-polished.

FIGS. 4A-C are illustrations, according to an embodiment of the present invention, of an object during various stages of polishing and the accompanying reflectivity histogram for determining an end-point for removing a material from an object. In FIG. 4A, object 410, containing a $SiO_2$ layer 408 and a copper layer 406, is shown before the CMP process begins. Incoming beam 404 from laser diode 201 interacts with the surface of the object 410 and the intensity of reflected beam 406 is proportional to the refractive index and the thickness of copper layer 406. A first histogram 412 displays the traditional reflectivity distribution for an unpolished sample 410 of pure copper.

In FIG. 4B, object 414, containing a $SiO_2$ layer 408 and a copper layer 406, is shown during the CMP process of removing copper layer 406. A second histogram 416 displays reflectivity distributions for an under-polished object 414 containing $SiO_2$ and copper. The width of the reflectivity distributions is not well defined and a significant peak reflectivity is not present within the distributions. An end-point for polishing has not been reached.

In FIG. 4C, object 418, containing a $SiO_2$ layer 408 and a copper layer 406, is shown after a relatively optimal CMP process of removing copper layer 406. A third histogram 420 displays reflectivity distributions for a substantially polished object 418 containing $SiO_2$ and copper. The width of the reflectivity distributions is well defined and a significant peak reflectivity is present within the distributions. An end-point for polishing has been reached.

Figure 5A:
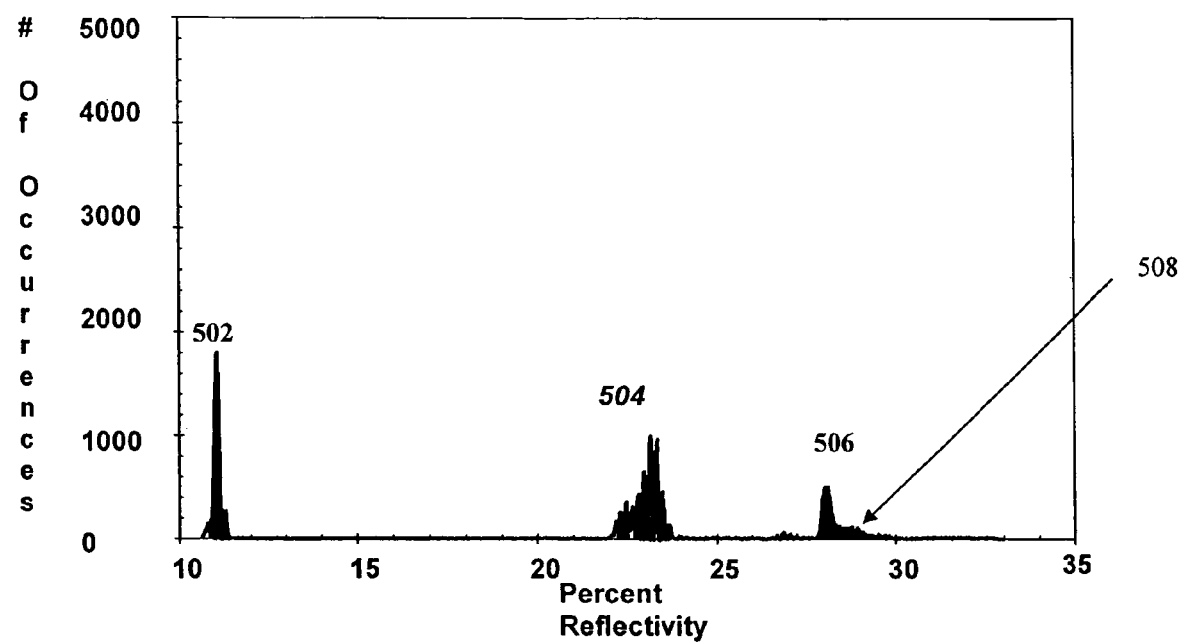
FIGS. 5A-5C are peak reflectivity histograms used to determine the end-point in the process of removing a layer of material by polishing in accordance with an embodiment of the present invention.
Figure 5B:
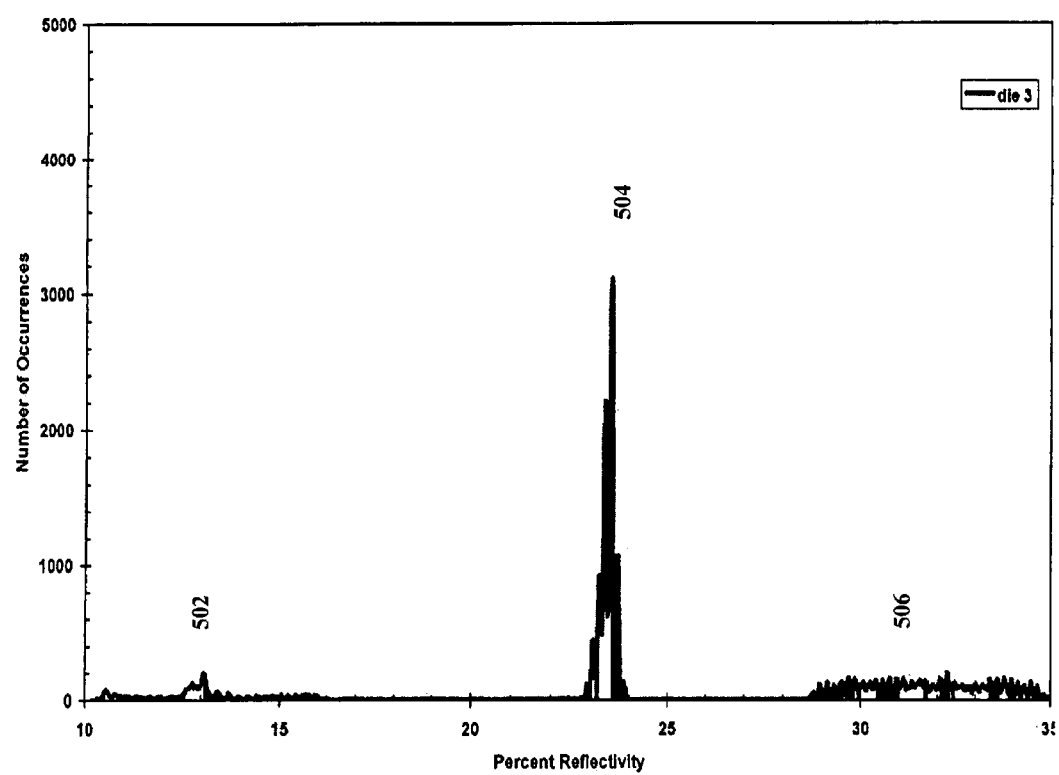
Figure 5C:
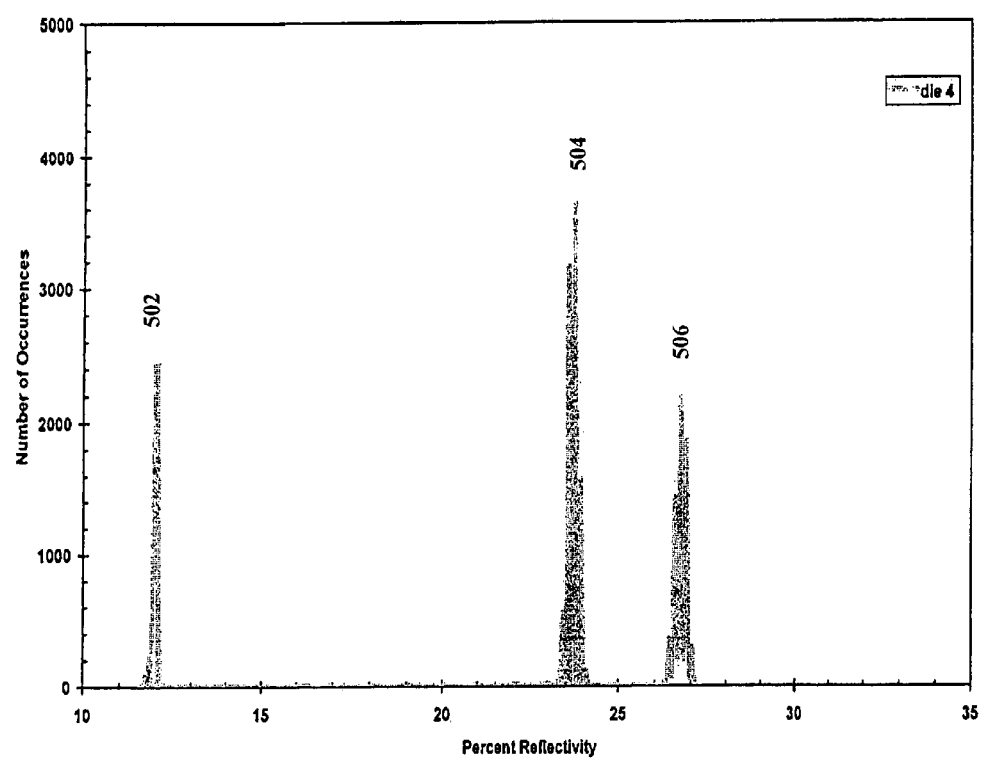

FIGS. 5A-C show the behavior of the histograms on a small area of different dies on a wafer with test patterns created to study the effect of CMP on small patterns on an unevenly polished wafer, according to an embodiment of the present invention. FIG. 5A illustrates a die that was under-polished and has a portion of copper left over. Reflectivity distributions (502, 504, and 506) are relatively well defined, however; the under-polished copper shows up as a wider spread in third distribution 506 and second distribution 504 and a smaller number of occurrences of second distribution 504. The wide spread of third distribution 506 is due to the presence of tail 508. FIG. 5B illustrates a die that was over-polished. This die was identified as over-polished due to the wider spread (as compared to FIG. 5A) for the third distribution 506, with the second distribution 504 remaining undisturbed. Also, a significant peak reflectivity was not found in FIG. 5B, therefore an end-point was not determined. FIG. 5C illustrates a die that was optimally polished, according to an embodiment. In this case, the all three distributions (502, 504, and 506) are sharp and distinct and have a very tight width.

While the invention has been particularly shown and described with reference to a preferred embodiment and various alternate embodiments, it will be understood by persons skilled in the relevant art that various changes in form and details can be made therein without departing from the spirit and scope of the invention.

The invention claimed is:

1. A method to manage a polishing operation on a surface of an object, comprising:
    generating a first reflectivity image of the surface of the object;
    generating a reflectivity histogram from the first reflectivity image of the surface of the object, wherein the reflectivity histogram measures a variation in the reflectivity of points on the surface of the object;
    analyzing the reflectivity histogram to determine whether a first peak of significant reflectivity is present within the histogram; and
    setting an end-point detection flag which indicates that the polishing operation has reached an end-point in the event that:
        a first peak of significant reflectivity is present within the histogram; and
        the first peak of significant reflectivity exceeds a predetermined threshold.

2. The method of claim 1, wherein generating a first reflectivity image of the surface of the object comprises:
    rotating the object about an axis;
    directing radiation from a radiation source onto the surface;
    collecting reflected radiation in a first position sensitive detector and a second position sensitive detector; and
    generating a first signal from the reflected radiation collected by the first position sensitive detector and generating a second signal from the reflected radiation collected by the second position sensitive detector; and
    summing the first signals and the second signals to generate an image of the surface.

3. The method of claim 1, wherein analyzing the reflectivity histogram to determine whether a first peak of significant reflectivity is present within the histogram comprises determining whether a reflectivity histogram exceeds a minimum number of occurrences.

4. The method of claim 3, wherein analyzing the reflectivity histogram to determine whether a first peak of significant reflectivity is present within the histogram comprises determining whether a point in a reflectivity histogram is higher than adjacent points.

5. The method of claim 1, further comprising terminating a polishing operation when the end-point detection flag is set.

6. The method of claim 1, further comprising setting an polishing flag which indicates that the polishing operation has reached an end-point in the event that:
    a first peak of significant reflectivity is not present within the histogram; or
    the first peak of significant reflectivity fails to exceed a predetermined threshold.

7. The method of claim 6, further comprising implementing a polishing operation when the end-point detection flag is set.

8. A system to manage a polishing operation on a surface of an object, comprising:
    an optical surface analyzer to generate a first reflectivity image of the surface of the object;
    a polishing analyzer comprising logic instructions stored in a computer readable medium which, when executed, configure a processor to:
        generate a reflectivity histogram from the first reflectivity image of the surface of the object, wherein the reflectivity histogram measures a variation in the reflectivity of points on the surface of the object;
        analyze the reflectivity histogram to determine whether a first peak of significant reflectivity is present within the histogram; and
        set an end-point detection flag which indicates that the polishing operation has reached an end-point in the event that:
            a first peak of significant reflectivity is present within the histogram; and
            the first peak of significant reflectivity exceeds a predetermined threshold.

9. The system of claim 8, wherein the optical surface analyzer:
    rotates the object about an axis;
    directs radiation from a radiation source onto the surface;
    collects reflected radiation in a first position sensitive detector and a second position sensitive detector; and
    generates a first signal from the reflected radiation collected by the first position sensitive detector and generating a second signal from the reflected radiation collected by the second position sensitive detector; and sums the first signals and the second signals to generate an image of the surface.

10. The system of claim 8, further comprising logic instructions stored in a computer readable medium which, when executed, configure a processor to determine whether a reflectivity histogram exceeds a minimum number of occurrences.

11. The system of claim 8, further comprising logic instructions stored in a computer readable medium which, when executed, configure a processor to determine whether a point in a reflectivity histogram is higher than adjacent points.

12. The system of claim 8, further comprising logic instructions stored in a computer readable medium which, when executed, configure a processor to terminate a polishing operation when the end-point detection flag is set.

13. The system of claim 8, further comprising logic instructions stored in a computer readable medium which, when executed, configure a processor to implement a polishing operation when the end-point detection flag is set.

14. The system of claim 8, further comprising logic instructions stored in a computer readable medium which, when executed, configure a processor to set a polishing flag which indicates that the polishing operation has reached an end-point in the event that:

a first peak of significant reflectivity is not present within the histogram; or the first peak of significant reflectivity fails to exceed a predetermined threshold.

* * * * *